(12) United States Patent
Hickman et al.

(10) Patent No.: US 6,921,834 B2
(45) Date of Patent: Jul. 26, 2005

(54) CONTINUOUS PROCESS FOR PREPARING N-PHOSPHONOMETHYL GLYCINE

(75) Inventors: Daniel A. Hickman, Midland, MI (US); James W. Ringer, Midland, MI (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 10/301,407

(22) Filed: Nov. 21, 2002

(65) Prior Publication Data

US 2003/0229245 A1 Dec. 11, 2003

Related U.S. Application Data (60) Provisional application No. 60/382,434, filed on May 22, 2002.

(51) Int. Cl.[7] .................................................. C07F 9/28
(52) U.S. Cl. ........................................................ 562/17
(58) Field of Search ...................... 562/17, 16; 502/177

(56) References Cited

U.S. PATENT DOCUMENTS

| | | |
|---|---|---|
| 3,117,152 A | 1/1964 | Michaels |
| 3,160,632 A | 12/1964 | Toy et al. |
| 3,799,758 A | 3/1974 | Franz |
| 3,868,407 A | 2/1975 | Franz et al. |
| 3,950,402 A | 4/1976 | Franz |
| 3,969,398 A | 7/1976 | Hershman |
| 3,977,860 A | 8/1976 | Franz |
| 4,147,719 A | 4/1979 | Franz |
| 4,197,254 A | 4/1980 | Gaertner |
| 4,199,354 A | 4/1980 | Hinshaw et al. |
| 4,264,776 A | 4/1981 | Hershman et al. |
| 4,405,531 A | 9/1983 | Franz |
| 4,406,777 A * | 9/1983 | Melconian .................. 208/156 |
| 4,486,358 A | 12/1984 | Moser |
| 4,507,250 A | 3/1985 | Bakel |
| 4,582,650 A | 4/1986 | Felthouse |
| 4,624,937 A | 11/1986 | Chou |
| 4,696,772 A | 9/1987 | Chou |
| 5,179,228 A | 1/1993 | Martin Ramon et al. |
| 5,470,748 A | 11/1995 | Hayden et al. |
| 5,942,643 A | 8/1999 | Farmer et al. |
| 5,962,729 A | 10/1999 | Hayden et al. |
| 6,022,993 A | 2/2000 | Cicha et al. |
| 6,054,612 A | 4/2000 | Cicha et al. |
| 6,342,129 B1 | 1/2002 | Vaughn et al. |

FOREIGN PATENT DOCUMENTS

| | | |
|---|---|---|
| EP | 0019445 A2 | 11/1980 |
| WO | WO 96/38455 | 12/1996 |
| WO | WO 01/92272 A2 | 6/2001 |

OTHER PUBLICATIONS

US 6,337,298, 1/2002, Ebner et al. (withdrawn)
CA:130:313453 abs of Journal of Catalysis by Pinel et al 182(2) pp 515–519 1999.*
CA:106:19046 abs of BR 8406213 Jul. 1986.*
CA:125:143008 abs of DE19500121 Jul. 1996.*
Pinel, C. et al: "Effect of the Nature of Carbon Catalysts on Glyphosate Synthesis", *Journal of Catalysts*, vol. 182, No. 2, Mar. 10, 1999 pp. 515–519.

* cited by examiner

*Primary Examiner*—Paul A. Zucker
(74) *Attorney, Agent, or Firm*—Craig Mixan (57) ABSTRACT

In general the present invention relates to a continuous process for manufacturing (N-phosphonomethyl) glycine, glyphosate, by the catalyzed oxidation of N-phosphonomethyliminodiacetic acid. Glyphosate can be provided in high yield and in a cost efficient process by minimizing the competing side reactions and by-products. The process includes conducting the oxidation reaction and selecting an appropriate catalyst to maximize the rate of the oxidation of N-phosphonomethyliminodiacetic acid while at the same time minimizing the rate of oxidation of glyphosate in the same reaction.

19 Claims, 3 Drawing Sheets

CONTINUOUS PROCESS FOR PREPARING N-PHOSPHONOMETHYL GLYCINE

CROSS-REFERENCE TO RELATED APPLICATION

The present application claims the benefit of U.S. Provisional Application Ser. No. 60/382,434 filed on May 22, 2002.

BACKGROUND OF THE INVENTION

The present invention relates to the preparation of glyphosate, N-phosphonomethyl glycine, by the catalyzed oxidation of N-phosphonomethyliminodiacetic acid.

The synthesis of glyphosate (PMG) by oxidation of N-phosphonomethyliminodiacetic acid (PMIDA) over a catalyst appears, at least on the surface, to be relatively straightforward. However, this reaction can be prone to vagaries that are particularly vexing to chemists. Part of the complexity lies in the identification, selection, and preparation of a suitable catalyst, and part of the complexity lies in the competing side reactions, which generate by-products. In addition, when a product such as PMG is selected for commercialization, the complexity of these problems and the number of potential solutions to the problems are multiplied. Well over 250,000 metric tons of glyphosate are sold annually. The production costs, including costs of starting materials, time, energy requirements, purification, waste management, and of course product yield, take on an even greater consideration.

While there have been significant advances in catalyst research, much about the specific catalysts, their properties, and their roles in a particular reaction remains a mystery. For this particular reaction, a wide variety of catalysts have been investigated. Each catalyst appears to have at least some advantages and, notably, significant disadvantages. For example, a carbon supported noble metal catalyst useful for oxidizing PMIDA is disclosed in U.S. Pat. No. 3,950,402. These catalysts tend to leach noble metals into the reaction solution under the reaction conditions. Each of U.S. Pat. Nos. 4,147,719, 5,179,228, WO 01/92272, and U.S. Pat. No. 6,337,298 discloses the use of different carbon supported noble metal catalysts that were treated to reduce noble metal leaching. However, the carbon supported noble metal catalysts are costly to prepare and the spent catalysts are expensive to recycle and treat. Furthermore, the carbon supported noble metal catalysts still generate side products in the oxidation reaction. Use of an activated carbon catalyst without any noble metals (or co-catalysts) in the PMIDA oxidation reaction is disclosed by Hershman in U.S. Pat. No. 3,969,398. The carbon catalyst produced relatively high yields of PMG in a batch reactor. However, the yields were lower in a continuous flow fixed bed reactor.

There continues to be research for improved catalysts and for methods of evaluating the different catalysts. For example, Cho in U.S. Pat. No. 4,624,937 and U.S. Pat. No. 4,696,722 disclosed carbon catalysts that were prepared by removing oxides from the carbon surface at high temperatures to form a highly reduced and a more highly activated carbon catalyst. Different methods have been used to evaluate the activity of a particular catalyst. For example, the decomposition of hydrogen peroxide by activated carbons was described in the literature at least as early as 1966 [R. N. Smith, et al., Trans. Faraday Soc., 62, 2553–2565 (1996)]. Activated carbons can be characterized by measuring the rate of hydrogen peroxide decomposition over these materials [K. H. Radeke, et al., Acta Hydrochim. Hydrobiol., 17, 315–319 (1989)]. Hayden et al. in U.S. Pat. No. 5,470,748 describes a specific method for measuring the catalytic activity of pulverized carbonaceous chars by measuring the time required for each to decompose a given quantity of hydrogen peroxide.

This peroxide procedure was subsequently used by Hayden et al. in U.S. Pat. No. 5,962,729 and by Farmer et al. in U.S. Pat. No. 5,942,643 to evaluate carbonaceous char useful for the oxidation of PMIDA to PMG. These references conclude that a highly reduced, fine particulate (particles smaller than 325 mesh; <44 $\mu$m) carbonaceous char exhibits high catalytic activity. The highly reduced carbonaceous char was used in a batch process to oxidize PMIDA to PMG as well as to produce carbon dioxide, presumably by oxidizing the formaldehyde and formic acid by-products from the oxidation reactions. However, no yields of PMG are disclosed. Furthermore, the reaction selectivity for PMG over the by-products such as (aminomethyl)phosphonic acid (AMPA), N-methyl-N-(phosphonomethyl)glycine (MePMG), or (methylaminomethyl)phosphonic acid (MAMPA) is not disclosed.

In WO 01/92272 various catalysts and processes for the production of PMG are described. The processes include oxidizing PMIDA over a carbon supported catalyst in a series of back-mixed zone reactors, fluidized bed reactors and/or fixed bed reactors. Different types of catalysts were specifically selected for use in the different reactors. For example, in a fixed bed reactor the carbon catalysts were selected to be highly active, particulate carbon-supported catalysts, extruded carbon supported catalysts, or non-conventional fixed bed catalyst supports, such as a monolithic screens or honeycomb supports. Additionally, the carbon supports can include one or more noble metals and optionally other metals deposited on the carbon. The highly active catalysts were used to further oxidize the formaldehyde and formic acid by-products to carbon dioxide and water. This reference did not provide any results demonstrating that high yields of PMG could be obtained in a fixed bed reactor. Furthermore, as mentioned above, the highly active catalysts and the noble metal carbon supported catalysts are expensive to produce and tend to leach noble metals into the reaction solution unless additional precautions are observed.

The reaction conditions for the oxidation of PMIDA can also greatly influence the yield of PMG and mixture of by-products. The yield of PMG can be low because of incomplete conversion of the PMIDA. Alternatively, if PMIDA is completely consumed, the yield of PMG can be low because of competing side reactions that produce a number of by-products such as (aminomethyl)phosphonic acid (AMPA) or formaldehyde and formic acid, which in turn are thought to be involved in the methylation of PMG and AMPA to yield N-methyl-N-(phosphonomethyl)glycine (MePMG) and (methylaminomethyl)phosphonic acid (MAMPA).

In some aspects PMG can be considered as an intermediate in a series of reactions from PMIDA to AMPA or the methylated product MAMPA. These competing series of reactions can lower the yield of the desired PMG product as well as make purification procedures and waste treatment processes more time consuming and costly. Again, the economic and environmental considerations for the large scale, commercially viable production of PMG require that the reaction provide a single, readily isolable product.

When a large scale production of a product is contemplated, it is typically considered that a continuous process provides economical advantages over a batch process. Using a fixed bed reactor in the continuous process can provide additional advantages. The total reactor volume for a fixed bed process is usually reduced relative to that required for a batch or continuous slurry process. In addition to the corresponding reduction in capital expense, a process using a fixed bed reactor is less labor intensive. Catalyst expenses will also be less for a continuous, steady-state fixed bed process as opposed to a slurry process where catalyst filtration and recycle are required.

In light of the above described problems, there is a continuing need for advancements in the relevant field, including improved synthetic methods to produce PMG using a environmentally sound process, and considering efficiency and economics to provide quantities of PMG suitable for commercialization via large scale production. The present invention is such an advancement and provides a wide variety of benefits and advantages.

SUMMARY OF THE INVENTION

In general the present invention relates to preparation of PMG. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a process for the production of glyphosate (PMG). The process comprises contacting N-phosphonomethyliminodiacetic acid (PMIDA) with molecular oxygen in the presence of a carbon catalyst supported in a fixed bed reactor under conditions that oxidize PMIDA to PMG. Under selected reaction conditions, PMG can be further oxidized to (aminomethyl) phosphonic acid (AMPA). The reaction conditions and carbon catalysts for use in the process are selected where the reaction rate of PMG oxidation is significantly less than the reaction rate of PMIDA oxidation. Preferably, the process is conducted such that a ratio of a rate constant of the reaction of glyphosate with molecular oxygen to a rate constant of the reaction of PMIDA with molecular oxygen is less than about 0.017.

In preferred forms, the present invention includes the selection of activated carbon catalysts such that PMIDA can be converted by oxidation to PMG in high yields in a continuous process. More specifically, the present invention concerns a continuous process for the production of PMG which comprises contacting an aqueous solution of PMIDA with a molecular oxygen containing gas in a fixed bed reactor at a temperature sufficiently elevated to initiate and sustain the reaction in the presence of a catalyst consisting of an activated carbon having a minimum particle size of about 150 to a maximum particle size of about 3000 micrometers ($\mu m$) and having physical and chemical properties which give acceptably low levels of undesirable AMPA.

DETAILED DESCRIPTION OF THE INVENTION

For the purposes of promoting an understanding of the principles of the invention, reference will now be made to the embodiments illustrated herein, and specific language will be used to describe the same. It will nevertheless be understood that no limitation of the scope of the invention is thereby intended. Any alterations and further modifications in the described processes, systems or compositions, and any further applications of the principles of the invention as described herein, are contemplated as would normally occur to one skilled in the art to which the invention relates.

In general, the present invention is directed to a process for continuously producing N-phosphonomethyl glycine or glyphosate (referred to herein as "PMG") from N-phosphonomethyliminodiacetic acid (referred to herein as "PMIDA"). The process comprises selectively oxidizing PMIDA in the presence of a carbon catalyst to produce PMG. In preferred embodiments, the process provides PMG in high yield, based upon the amount of PMIDA consumed, and in high purity, by minimizing the generation of by-products that would otherwise diminish PMG yield. The relevant oxidation reaction of PMIDA is illustrated below in Equation 1.

(1)

An aqueous solution of PMIDA starting material and oxygen are placed in contact with a selected carbon catalyst "C" to produce PMG. The initial oxidation reaction also produces of a mixture of $CO_2$ and formaldehyde as by-products. However, once PMG is generated in the reactor, it can react with oxygen over the catalyst to yield (aminomethyl)phosphonic acid (referred to herein as "AMPA") as shown below in Equation 2. Again, the reaction produces a mixture of $CO_2$ and formaldehyde by-products.

(2)

In one aspect, the desired product, PMG, can be considered as an intermediate in the two reaction processes illustrated above; AMPA, in effect, is the over-oxidized by-product. One method of producing a high yield of the desired PMG product would be to maximize the rate of reaction of PMIDA with oxygen to produce PMG as shown in Equation 1, while at the same time either minimizing or stopping the rate of reaction of the intermediate PMG with oxygen, shown in Equation 2.

In addition to the catalyzed oxidation reactions illustrated above, PMG can also undergo non-catalyzed reactions. For example, PMG can react with other reaction by-products, such as formic acid and/or formaldehyde produced either in the initial PMIDA oxidation reaction or the oxidation reaction of PMG. Formic acid and formaldehyde are referred to herein as C1 reaction by-products. Either of these C1 reaction by-products can methylate PMG to generate N-methyl-N-(phosphonomethyl)glycine (referred to herein as "MePMG") as illustrated below in Equation 3.

(3)

Under the oxidation reaction conditions, MePMG can be oxidized to yield (methylaminomethyl)phosphonic acid (referred to herein as "MAMPA") as shown below in Equation 4.

(4)

Additionally the over-oxidized by-product, AMPA, can undergo methylation to generate MAMPA, illustrated below in Equation 5.

(5)

Formic acid can be formed by partial oxidation of formaldehyde over the carbon catalysts in any of the above reactions. The net reaction scheme or profile can be illustrated as shown below in Equation 6.

(6)

To maximize the yield of PMG and minimize competing side reactions, it would be preferable to select reaction conditions, including catalyst preparation/selection, to increase or maintain a high rate of PMIDA conversion to PMG while at the same time ensuring a much slower rate of PMG conversion to the various by-products through the alternate reaction pathways.

Figure 1:
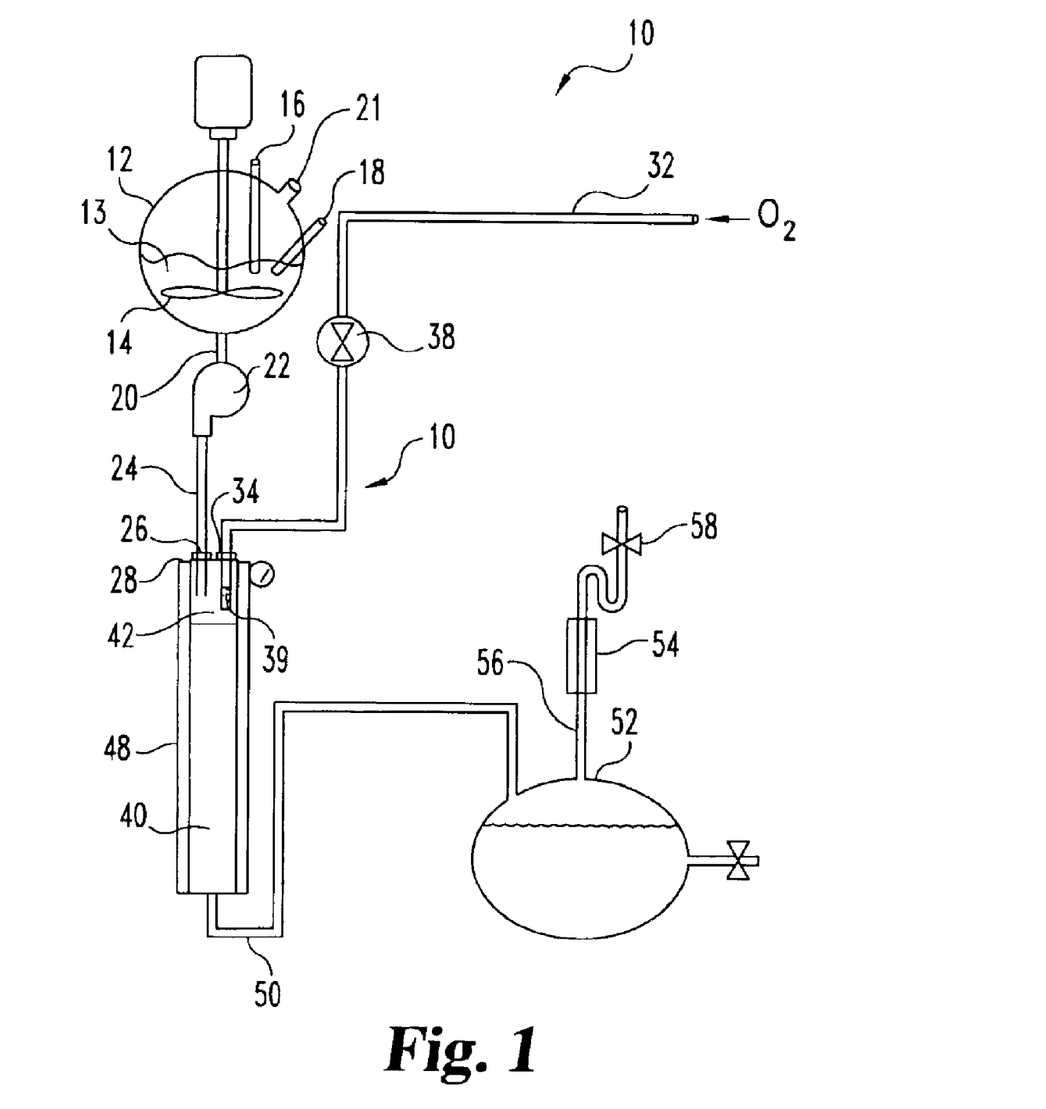
FIG. 1 is a diagram of one embodiment of a fixed bed reactor system for use with the present invention.

The oxidation reaction of PMIDA can be performed in a single fixed bed reactor as illustrated in FIG. 1. Reactor system 10 includes a mixing vessel 12 for the PMIDA feed stream. Mixing vessel 12 includes a stirring mechanism such as a paddle 14. It should be understood that alternative stirring and mixing devices, such as a blade, bar or the like, can be used in mixing vessel 12. It is preferable that the reaction mixture in mixing vessel 12 be maintained as a homogenous mixture, and consequently, ensure that the reactant feed stream is homogeneous. A heater 16 and a temperature sensor 18 are used to maintain the reaction mixture 13 in mixing chamber 12 at a desired temperature level. Mixing vessel 12 also includes a sampling port 21 allowing access to the reaction mixture 13.

Line 20 leads from mixing vessel 12 to a pump 22. From pump 22 an inlet line 24 leads to injection port 26 on top of reactor 28. Inlet line 24 optionally can include metering valve positioned between pump 22 and injection port 26. Oxygen feed line 32 provides a conduit for an oxygen containing gas to injection port 34 on top of reactor 28. Oxygen feed line 32 can include a mass flow controller 38. Sparge line 39 extends from injection port 34 into reactor 28 providing oxygen to top of catalyst bed 40. In alternative embodiments, oxygen feed line 32 and inlet line 24 can join together before entering into reactor 28. In still other alternative embodiments, oxygen feed line 32 and/or inlet line 24 can enter the bottom of reactor 28.

Reactor 28 is illustrated as a fixed bed reactor charged with a carbon catalyst. A head space 42 is provided on top of catalyst bed 40. For a reactor of large diameter (approximately greater than one inch), a liquid or gas-liquid distributor should be included in head space 42 to achieve a radially uniform distribution of the liquid at the top of the catalyst bed. In one embodiment, reactor 28 includes a jacket 48 to maintain desired temperature level. In addition, one or more of the inlet lines or associated equipment providing reactants to the reactor can be insulated and/or heated; such lines and associated equipment include, without limitation: mixing vessel 12, line 20, inlet line 24, oxygen feed line 32, sparge line 39, and pump 22.

Exit line 50 from the bottom of reactor 28 provides a conduit for the effluent containing the reaction products to reservoir 52 where the effluent can be stored or further processed, for example to separate the desired product from water. Reservoir 52 can include vent line 56, condenser 54, and back pressure regulator 58 to help maintain the desired pressure in reactor 28 and allow venting of unreacted oxygen, water vapor and gaseous by-products as desired. Alternatively, reservoir 52 can be simply a lower section of the reactor vessel, reactor 28, where the gas-liquid separation zone represented by reservoir 52 is below the catalyst bed support grid.

In use, an initial aqueous solution of PMIDA is thoroughly mixed in mixing vessel 12 to ensure that the PMIDA feed stream is homogeneous before being transferred through line 24 to the headspace 42 of reactor 28. Additionally, a filter can be placed between vessel 12 and injection port 26 to collect and prevent any solid particles that may be in the reaction mixture from entering reactor 28. The initial concentration of PMIDA in the feed stream can be predetermined or more preferably preselected for use in the kinetic studies considering the temperature level employed for the reaction. Oxygen from sparge line 39 enters headspace 42 of reactor 28. The reaction pressure can be established using mass flow controller 38 in conjunction with back pressure regulator 58. The oxygen flow rate can be established using mass flow controller 38. Additionally, pump 22 can be adjusted to provide the desired flow rate of the PMIDA feed stream to reactor 28.

Once in the reactor, the oxygenated PMIDA feed stream is forced through the catalyst bed 40. The oxygenated PMIDA feed stream undergoes oxidation in the presence of the carbon catalyst as the feed stream percolates through the catalyst bed 40. The resulting mixture emerges as an effluent stream from the bottom of reactor 28. Exit line 50 provides a conduit to transfer the effluent to reservoir 52.

In a preferred embodiment, the production of PMG according to the present invention can be accomplished by continuous feeding of both a molecular oxygen containing gas and an aqueous solution of PMIDA through a fixed bed reactor containing an activated carbon catalyst. A more preferred manner of operation involves conducting the catalyzed oxidation reaction under plug flow conditions using the fixed bed reactor.

The reactants, oxygen and PMIDA, can be admixed into a single feed stream prior to entering the reactor. The resulting feed stream can enter at the top of the reactor and flow downward or enter at the bottom of the reactor and flow upward. Alternatively, oxygen and PMIDA can enter the reactor in separate feed streams. Once in the reactor, the feed streams can either flow in the same direction or in counter directions through the reactor. The preferred mode of operation involves a co-current downflow of reactant streams through the fixed bed reactor. By a judicious selection of the reaction conditions, the overall yield and selectivity of PMG can be increased while the side reactions and generation of by-products such as AMPA can be minimized.

As it will be become apparent from the below discussion, many of the reaction conditions are interrelated such that a change in one reaction parameter can effect a change in the reaction that can be countered or enhanced by manipulating a different reaction parameter.

The temperature level employed for the process should be sufficient to initiate the PMIDA oxidation reaction and to sustain that oxidation reaction once initiated. It has been determined that the carbon catalyzed reaction of PMIDA with oxygen to generate PMG is exothermic. Consequently, the reaction temperature should be carefully monitored and/or controlled as the reaction progresses. At lower reaction temperatures, the rate of PMIDA oxidation may be undesirably slow. Further, it is thought that under certain conditions, at higher temperatures, over-oxidation of PMG to AMPA begins to be a significant side reaction. The preferred reaction temperature level is also dependent upon the catalytic activity of the selected catalyst. For example, a less active catalyst may require a higher reaction temperature level either to initiate the oxidation reaction or to sustain that oxidation reaction and provide the same PMIDA conversion rate similar to that observed using a more highly active catalyst.

In the preferred embodiment, the fixed bed reactor is operated adiabatically, with reactor jacket 48 replaced by a layer of insulation to minimize heat losses from the vessel. Because adiabatic operation will result in a temperature rise due to the exothermic nature of PMIDA oxidation, a higher initial PMIDA concentration will result in a higher temperature rise at complete conversion of PMIDA. In cases where this temperature rise is too high, leading to undesirable catalyst performance, it may be necessary to provide heat removal in order to reduce the maximum temperature in the catalyst bed. This can be achieved using one of several reactor design schemes known to those skilled in the art. Examples of suitable design schemes can be found in O. Levenspiel, *The Chemical Reactor Omnibook,* OSU Bookstores, Inc., Corvallis, Oreg. (1993), which is incorporated herein by reference. These reactor design schemes include, but are not limited to the following: (1) a series of reactors with interstage cooling (by heat exchange with a cooling medium or by cold-shot injection of a cool feed mixture); (2) a single reactor with partial recycle of the effluent, which is cooled before it is combined with the fresh makeup feed stream or is cooled by mixing with a cold fresh makeup feed stream; (3) a combination of the first two schemes, where one or more of the reactors in a series are cooled by partial recycle of cooled effluent; (4) a wall-cooled reactor, where heat exchange with a cooling medium is provided within the catalyst bed.

The reaction temperature level (and the temperature level of a PMIDA containing feed stream) affects the solubility of PMIDA in water. Increasing the temperature level increases the solubility of PMIDA in water. This in turn increases the amount of dissolved PMIDA that can be introduced into the reactor. It has been determined that at low PMIDA concentrations, the rate of the catalyzed oxidation of PMIDA is dependent on the PMIDA concentration, while at high PMIDA concentrations the catalyzed oxidation rate is independent of the PMIDA concentration. Additionally, the oxidation rate and operation of the reactor can be dependent upon the solubility of PMIDA. It is preferable to eliminate any undissolved or suspended PMIDA particles in the reactor. The solid particles deposit on the catalyst in the reactor to reduce flow and eventually clog a fixed bed reactor. Consequently, it is highly desirable to maintain the PMIDA in solution. Further, from an economical consideration, a higher concentration of PMIDA affords a higher concentration of PMG in the effluent from the reactor and reduces the amount of water that must be recycled and/or treated from the reaction.

It is preferred that the reactant feed stream(s) be heated to approximately the same temperature level or below the desired reaction temperature level. Since the catalyzed PMIDA oxidation reaction is exothermic once initiated, the oxidation reaction will generate additional heat energy. Some of the heat energy generated from the oxidation reaction can be adsorbed by the entering reactant feed stream(s). However the temperature of the reactant feed stream should not be so low as to induce inhomogeneity in the reaction vessel or to limit PMIDA solubility.

Preferably, the temperature level for conducting the reaction can be selected to be at least about 25° C., and more preferably at least about 75° C. For practical applications, it is preferable that the temperature level be less than or equal to about 180° C., and more preferably less than or equal to about 150° C.

The pressure under which the process is conducted can vary over wide ranges. The reaction is preferably run under positive pressure relative to atmospheric pressure. Additionally, the inlet pressure to the reaction vessel should be sufficient to provide the desired flow rate through the catalyst bed. The desired pressure can vary depending upon a number of factors including, but not limited to: the catalyst particle size, the diameter and/or length of the catalyst bed, the temperature level of the reaction mixture in the reaction vessel, and the desired concentration of oxygen and/or oxygen containing gas. Generally as the catalyst particle size decreases, greater pressure is needed to maintain the same flow rate through the reactor at the same bed exit pressure compared to a reactor packed with larger sized catalysts. Similarly, greater pressure is required to achieve the same flow rate through the longer catalyst bed as through the shorter catalyst bed of the same diameter at the same bed exit pressure. Conversely, a reactor with a larger diameter catalyst bed can use lower pressure to achieve substantially the same flow rate as a smaller diameter catalyst bed of the same volume of catalyst at the same bed exit pressure. Furthermore, at temperatures above 100° C., higher pressures must be applied to the system to maintain the water in the liquid phase.

Since one of the reactants, oxygen, is a gas, increasing the pressure increases the concentration of dissolved oxygen in the reaction mixture. The concentration of dissolved oxygen is dependent upon the partial pressure of oxygen in the reaction mixture. Increasing the pressure will increase the partial pressure of oxygen, thereby increasing the liquid phase concentration of dissolved oxygen. Conversely, decreasing the pressure will decrease the partial pressure of oxygen—and the concentration of dissolved oxygen.

The pressure of the reaction can be regulated by controlling the flow rate of the vapor stream leaving the reactor or a downstream vapor-liquid separator. While not critical for the present invention, the pressure in the reactor is typically maintained from a minimum of about 1 atmosphere (atm) (0.1 megapascals, MPa), more preferably at a minimum of about 2 atm (0.2 MPa), still yet more preferably at a minimum of about 3.5 atm (3.5 MPa). Preferably, the maximum pressure is selected to be less than about 100 atm (10 MPa), more preferably less than about 20 atm (2 MPa).

The term molecular oxygen containing gas, as used herein, means any gaseous mixture containing molecular oxygen with, optionally, one or more diluents, which are non-reactive with the oxygen, with the reactant, and the desired product under conditions of the reaction. Examples of such gases include air, oxygen diluted with helium, argon, nitrogen or other inert gas, and the like. It is preferred to employ gases containing at least about 20% by weight molecular oxygen. The higher the concentration of oxygen in the gas, the higher the partial pressure and concentration of dissolved oxygen in the reaction mixture.

The relative amount of molecular oxygen employed for the process can vary over wide ranges. The catalytic reaction rate is a function of the dissolved oxygen concentration. If the dissolved oxygen concentration is sufficiently high, the oxidation reaction rate is independent of the oxygen concentration. However, if the oxygen concentration is low, the oxidation reaction rate is dependent on the oxygen concentration. In either case, the dissolved oxygen concentration at any axial position in the reactor is directly proportional to the oxygen partial pressure, in accordance with Henry's Law. The preferred process is run at or near complete conversion of the PMIDA. Under these conditions, at least a stoichiometric amount of oxygen is employed, i.e., at least 0.5 mole of oxygen per mole of PMIDA. However, the efficiency of oxygen utilization in the oxidation reaction is usually less than 100 percent. Furthermore, the carbon dioxide by-product reduces the partial pressure of oxygen in the gas phase and, consequently, the concentration of dissolved oxygen. Thus, additional oxygen above the stoichiometric amount is required to give nearly complete conversion of PMIDA and to maintain desired conversion rates at the end of the bed. Conversely, maintaining an oxygen feed rate near the stoichiometric amount, i.e., about 0.5 moles of oxygen per mole of PMIDA, can prevent excessive over-oxidation of PMIDA to AMPA and can minimize the resulting pressure drop across the catalyst bed. In order to optimize the trade-off between these competing factors, the amount of oxygen employed should be in slight excess. The amount of oxygen employed will be at least about 0.5 molar equivalents, most preferably at least about 0.7 molar equivalents based upon the moles of PMIDA. In preferred embodiments the amount of oxygen employed will be less than about 10 molar equivalents of oxygen, more preferably less than about 5 molar equivalents of oxygen, again based upon the moles of PMIDA added to the reaction. Higher molar ratios of oxygen to PMIDA need not be detrimental as long as the resulting pressure drop across the catalyst bed is acceptable and other reactor parameters, including pressure, temperature, and feed rate, are adjusted to avoid excessive over-oxidation of PMG to AMPA while maintaining nearly complete PMIDA conversion.

The liquid hourly space velocity (LHSV, the liquid volumetric feed rate divided by the catalyst bed volume) of the reactants flowing through the catalyst bed should be selected so that all or nearly all of the PMIDA is oxidized to PMG upon exiting the reaction vessel and so that over-oxidation of PMG to AMPA is minimized. The optimal LHSV can be dependent upon a variety of parameters, including, but not restricted to: the oxygen partial pressure, the temperature of the catalyst bed, the activity of the catalyst, and the concentration of PMIDA and other components in the feed solution. In preferred embodiments, the LHSV in the fixed bed reactor is selected to provide a low rate of PMG oxidation relative to a rate of PMIDA oxidation.

The LHSV usually is increased for smaller sized catalyst particles. The smaller sized catalyst particles typically promote the conversion of PMIDA to PMG at faster rates per unit volume in a fixed bed reactor. Consequently, the complete conversion of PMIDA occurs more rapidly.

In conducting the process, it is preferred to employ nearly saturated solutions of PMIDA in water at the desired temperature level of the reaction. Additionally, higher concentrations of PMIDA can significantly enhance the ease of operation, recovery of product, and reduce of the amount of effluent that is recycled or treated. The solubility limit of PMIDA in water at 75° C. is about 2 percent by weight (wt %), based upon the weight of the resulting solution. The solubility of PMIDA increases with temperature. For example, PMIDA has a solubility of about 6 wt % at about 105° C. Additionally, the PMIDA solubility can be increased by the addition of base, e.g., sodium hydroxide or isopropylamine to form the highly water soluble salt of PMIDA. In preferred embodiments, the concentration of PMIDA in the feed stream for the oxidation reaction is selected to be between about 2 wt % and about 10 wt %.

The amount of a catalyst used in the oxidation reaction can vary. In preferred embodiments, the desired amount of catalyst used in the oxidation reaction can be dependent upon the catalyst activity, average catalyst particle size, oxygen partial pressure, reaction temperature, feed mixture composition, and PMG production capacity.

The activated carbon catalysts useful as catalysts for this invention have a particle size range from a minimum of about 150 $\mu$m (100 mesh) to a maximum of about 3000 $\mu$m (6 mesh), preferably from a minimum of about 250 $\mu$m (60 mesh) to a maximum of about 1000 $\mu$m (18 mesh). In a fixed bed reactor, larger particles of a given carbon catalyst tend to give inferior yields of PMG due to increasing over-oxidation to AMPA, while smaller particles tend to increase pressure drop across the catalyst bed beyond acceptable limits. Examples of commercially available catalysts are listed below in Table 1.

TABLE 1

Commercially Available Carbon Catalysts

| Carbon Catalyst | Approx. Mesh Size | Approx. particle size range ($\mu$m) | Packed Bulk Density (g/cm$^3$) | Carbon Source |
|---|---|---|---|---|
| Calgon CENTAUR | 20 × 50 | 300–840 | 0.53 | Coal |
| Calgon BCP | 20 × 50 | 300–840 | 0.36 | Coal |
| Norit PK 0.25–1 | 18 × 60 | 250–1000 | 0.24 | Peat |
| Waterlink SE | 20 × 50 | 300–840 | 0.48 | Coconut shell |
| Waterlink 207A | 20 × 50 | 300–840 | 0.58 | Coal |

TABLE 1-continued

Commercially Available Carbon Catalysts

| Carbon Catalyst | Approx. Mesh Size | Approx. particle size range (μm) | Packed Bulk Density (g/cm³) | Carbon Source |
|---|---|---|---|---|
| Sibunit 6 | 35 × 70 | 200–500 | 0.65 | Gaseous hydrocarbons |
| Nuchar RGC | 20 × 50 | 300–840 | 0.29 | Wood |

The catalysts are selected to preferentially oxidize PMIDA to PMG. The properties of the catalyst have been found to influence the production of PMG. The activated carbon catalysts useful as catalysts for this invention are porous, and possess physical and chemical properties. These properties include the intrinsic catalytic activity, the surface area, the pore volume, the pore size distribution, and the particle size. In one preferred embodiment, the catalyst is a carbon catalyst without any added or deposited metals. Alternatively, a carbon catalyst with deposited metals can be used to minimize oxidation of formic acid and/or formaldehyde, which, in turn, reduces the rates of the methylation reactions, Equations 3 and 5. Regardless, the catalysts for the present invention are selected to exhibit a catalytic activity under the reaction conditions that yields an acceptable low yield of the over-oxidized product, AMPA, at high PMIDA conversion.

In a preferred embodiment, the reaction process is conducted under conditions to maintain the rate of reaction for the catalyzed oxidation of PMIDA to PMG sufficiently high, compared to the rate of reaction for the catalyzed oxidation of PMG to AMPA. In a fixed bed reactor, the primary reactions are the catalytic oxidation and non-catalyzed methylation reactions. The overall reaction scheme as described herein is illustrated below in Equation 7.

fixed bed reactor is relatively high. For example, in a selected reactor the LHSV generally can be on the order of 6 hr$^{-1}$ for a feed containing 6 wt % PMIDA. If the liquid holdup in the reactor is 30% of the total volume, this LHSV corresponds to an actual residence time of the liquid phase of only about 3 minutes. Consequently, the extent of the methylation reactions is exceedingly small compared with the extent of PMIDA oxidation. For practical purposes for the present invention, these non-catalytic side reactions can be ignored.

The progress of the reaction(s) can be monitored to evaluate the reaction rates by analyzing effluent from a fixed bed reactor such as the reactor illustrated in FIG. 1 to determine the concentration of the reactants and/or products, and determine the reaction kinetics for both the catalyzed oxidation of PMIDA to PMG and the catalyzed oxidation of PMG to AMPA.

In an alternative embodiment for gathering kinetic data, reservoir 52 can be eliminated and exit line 50 can be routed back to reservoir 12 so that the reactor effluent stream is returned to the feed reservoir. In this embodiment, vessel 12 can include a vent line, a condenser, and a back pressure regulator to help maintain the desired pressure in reactor 28 and allow venting of unreacted oxygen, water vapor and gaseous by-products as desired. Optionally, a back pressure regulator can be relocated to the exit line 50 so that reservoir 12 can be maintained at ambient pressure. In this alternative embodiment, the reaction effluent can be sampled at reservoir 12 or from exit line 50 at predetermined time intervals to determine the concentration of the reactants and products generated from the oxidation reaction. The samples for the reservoir 12 can be evaluated by a variety of methods. For example, the reaction can be followed by monitoring the concentrations of PMIDA, PMG, and AMPA in the effluent exit line 50 from the reactor or the reaction mixture in mixing vessel 12 over time. Preferably, the samples taken at (7)

The rate constant for catalyzed oxidation of PMIDA to PMG is listed as $k_1$. Similarly, the rate constant for the catalyzed oxidation of PMG to AMPA is listed as $k_2$; the rate constant for the methylation of PMG to MePMG is $k_3$; and the rate constant for the methylation of AMPA to MAMPA is listed as $k_4$. In preferred embodiments, the LHSV in a different time points are analyzed by gas or liquid chromatography. Preferably the reaction is continued until at least about 95 wt % of the PMIDA has been consumed, more preferably until at least about 98 wt % of the PMIDA has been consumed based upon the total initial weight of the PMIDA.

A commercially available program is used to solve the mass balance equations for each experimental data point. The model used to fit the experimental data was developed using the SIMUSOLV® computer program, a program for solving ordinary differential equations and determining best fit parameters. The program uses its built-in numerical techniques for solving ordinary differential equations (where appropriate) and optimizing the kinetic parameters in order to provide a "best-fit" based on some objective function. The SIMUSOLV® computer program uses maximum likelihood estimation to determine best-fit parameters. Other computer programs may use least squares or other regression techniques described in the literature.

The primary oxidation reactions occur almost exclusively on the catalyst. While not intending to be bound by any theory, it is thought that the majority of the oxidation reaction occurs within the pores in the catalysts. The observed rate, $r_1$, of the oxidation of PMIDA with oxygen, can be approximated using the rate expression illustrated below in Equation 8:

$$r_1 = \frac{k_{r1}[PMIDA][O_2]}{(1 + K_{PMIDA}[PMIDA] + K_{PMG}[PMG])} \quad (8)$$

where [PMIDA] and [PMG] are the bulk liquid phase concentrations, and [$O_2$] is the partial pressure of oxygen. The values of $k_1$, $k_2$, $K_{PMIDA}$ and $K_{PMG}$ are empirically derived from analysis of the kinetic analysis of an oxidation reaction for example as performed in a reactor as illustrated in FIG. 1.

A similar rate expression, listed below as Equation 9, was used for the conversion of PMG to AMPA:

$$r_2 = \frac{k_{r1}[PMG][O_2]}{(1 + K_{PMIDA}[PMIDA] + K_{PMG}[PMG])} \quad (9)$$

where [PMIDA], [PMG], $k_1$, $k_2$, $K_{PMIDA}$, and $K_{PMG}$ are as described above. These expressions lump any mass transfer effects which are a result of the catalysts' physical properties (intraparticle or interparticle) into the overall rate expression. To extract reaction kinetic parameters, $k_1$, $k_2$, $K_{PMIDA}$ and $K_{PMG}$, from the experimental data, a mass balance on the well-mixed pot was combined with a continuous single-pass fixed bed (plug flow) reactor. Such an approach has been described in the literature (N. Papayannako and J. Marangozis, Chem Eng. Sci., Vol. 39, No. 6, pp. 1051–1061, 1984). One could also generate kinetic data in a continuous single-pass fixed bed (plug flow) reactor as shown in FIG. 1. In that case, the steady state reactor performance would be simulated using the plug flow reactor equations. Similarly, one could generate kinetic data in a continuous stirred tank reactor (CSTR). In that case, a CSTR mass balance equation would be used in conjunction with the rate expressions.

For a given set of reaction conditions (temperature, pressure, concentrations), the relative rate of these two reactions reduces to Equation 10 listed below.

$$r_2/r_1 = k_2[PMG]/k_1[PMIDA] = \alpha[PMG]/[PMIDA] \quad (10)$$

It has been determined that the PMG selectivity correlates to the value of the ratio $\alpha$ ($\alpha = k_2/k_1$), with higher values of $\alpha$ giving lower selectivity to PMG (and higher selectivity to AMPA). For a plug flow or batch reactor where $\alpha$ is constant throughout the reactor (under isothermal conditions or conditions where the apparent activation energies for both reactions are identical), the molar selectivity to AMPA ($S_{AMPA}$), which is the moles of AMPA formed divided by the moles of PMIDA converted, is given by the Equation 11 listed below:

$$S_{AMPA} = [\alpha X_1 - 1 + (1 - X_1)^\alpha]/[X_1(\alpha - 1)] \quad (11)$$

where $X_1$ is the fractional conversion of PMIDA and a is as defined above. Thus, the performance of a carbon catalyst can be evaluated by determining the value of $\alpha$ for that carbon catalyst under the reaction conditions employed for the catalytic oxidation reaction. For example, a catalyst with $\alpha=0.017$ will give 6% AMPA selectivity at 99% PMIDA conversion. Likewise, at 99% PMIDA conversion, $\alpha=0.008$ gives 3% AMPA selectivity, and $\alpha=0.004$ gives 1.5% AMPA selectivity. The ratio $\alpha$ corresponds to the AMPA selectively (and consequently to the PMG selectivity) as graphically illustrated in FIG. 2.

Figure 3:
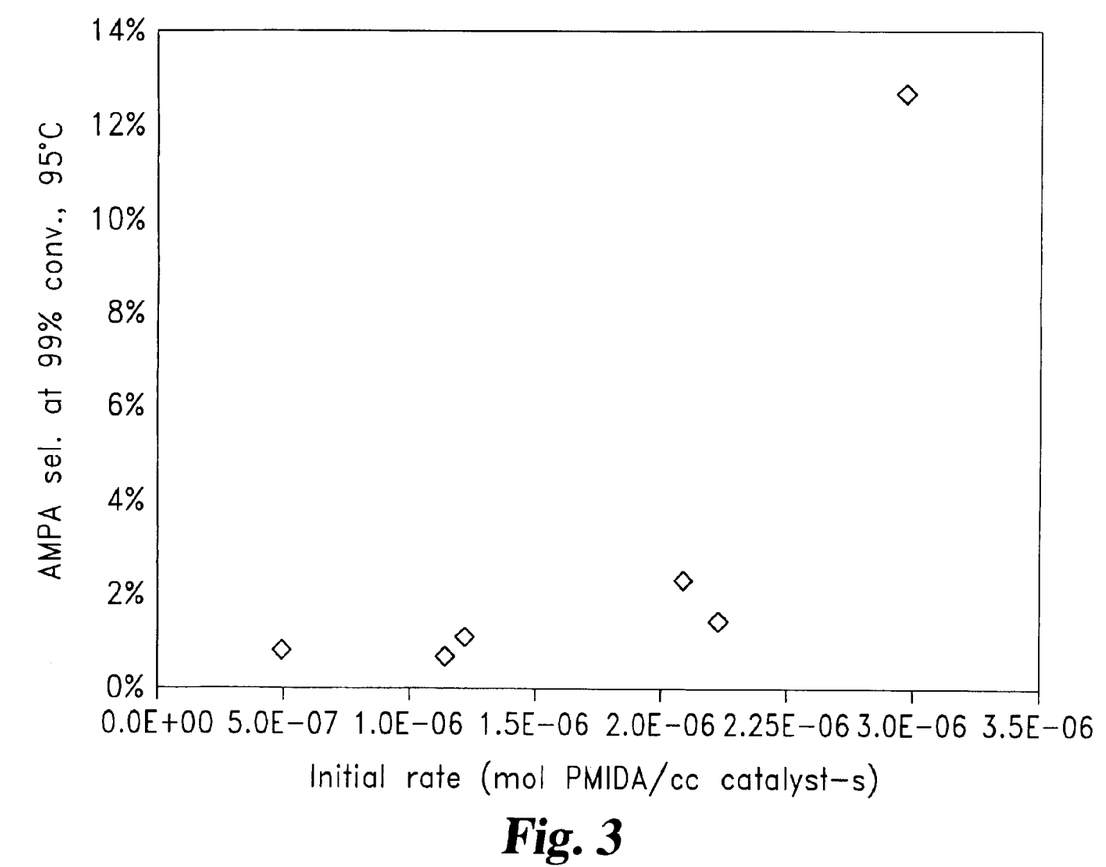
FIG. 3 is a graph illustrating the selectivity of AMPA versus the initial rate of PMIDA conversion in an oxidation reaction performed in accordance with the present invention.

The rate ratio $r_2/r_1$ is a ratio of observed rates for the two oxidation reactions. While not intending to be bound by any theory, it is thought that the rates are controlled, in part, by pore diffusion. Since the selectivity of PMG formation is essentially 100% at less than 70% conversion for all particle sizes evaluated, the intrinsic rate of PMIDA oxidation should be substantially higher than the intrinsic rate of PMG oxidation when PMIDA is present in the mixture. For a longer average pore length or higher catalyst intrinsic activity, the fraction of the pore length that is utilized for PMIDA oxidation decreases. Beyond this depth of PMIDA penetration, the only reactant available for oxidation is PMG. Thus, assuming both oxidation reactions utilize the same catalytic sites, carbons of the same particle size and pore structure should give higher maximum yields of PMG as the intrinsic catalyst activity decreases. This hypothesis is supported by the data in FIG. 3 where higher initial volumetric rates (measured for 2 wt. % PMIDA with no PMG at 95° C. and 90 psig (0.72 Mpa)) correlate with higher losses of PMG to AMPA at a fixed PMIDA conversion. The AMPA selectivity increases (PMG selectivity decreases) as the initial rate of PMIDA conversion per cc of carbon catalyst per second increases.

In preferred embodiments, the oxidation of PMIDA to PMG is conducted to provide a ratio of the rate constant of the oxidation reaction of PMG to the rate constant of the oxidation of PMIDA at less than about 0.017. More preferably, the oxidation of PMIDA to PMG is conducted to provide a ratio of the rate constant of the oxidation of the reaction of PMG to the rate constant of the oxidation of PMIDA at less than about 0.008, still more preferably less than about 0.004.

Furthermore, the molar yield $Y_{PMG}$ of PMG from PMIDA (moles PMG formed per mole PMIDA fed to the reactor) is defined as illustrated below in Equation 12:

$$Y_{PMG} = X_1(1 - S_{AMPA}) \quad (12)$$

where $Y_{PMG}$ is the molar yield of PMG. The maximum attainable yield of PMG occurs when the above equation is maximized with respect to $X_1$. This maximum yield occurs at the optimal PMIDA conversion defined by Equation 13 illustrated below:

$$X_{1,opt} = 1 - \alpha^{1/(1-\alpha)} \quad (13)$$

Table 2 lists the performance of seven carbon catalysts at 95° C. reactor temperature using the above-described catalyst activity. These data show that different carbons gave values of α that varied over a wide range, corresponding to a range of AMPA selectivities.

TABLE 2

| Carbon Catalyst | Mesh | α | AMPA selectivity at 99% PMIDA conversion | Maximum PMG yield* |
|---|---|---|---|---|
| Calgon CENTAUR | 20 × 50 | 0.0369 | 12.6% | 88.1% |
| Waterlink 207A | 20 × 50 | 0.0061 | 2.2% | 96.9% |
| Calgon BCP | 20 × 50 | 0.0039 | 1.4% | 97.9% |
| Norit PK | 18 × 60 | 0.0029 | 1.1% | 98.3% |
| Waterlink SE | 20 × 50 | 0.0028 | 1.0% | 98.4% |
| Sibunit 6 | 18 × 35 | 0.0021 | 0.7% | 98.7% |
| Nuchar RGC | 20 × 50 | 0.0018 | 0.6% | 98.9% |

*$Y_{PMG}$, calculated using Equation 12.

Carbons from wood, peat, coal, coconut shells, bones, lignite, petroleum-based residues, sugar, or organic polymers are suitable for the process of this invention provided that the ratio a is acceptably small and the particle size is from a minimum of about 150 μm to a maximum of about 3000 μm.

In alternative forms, the catalyst can be evaluated independently of the selected catalyzed oxidation reactions. For example, the peroxide decomposition method described by Hayden et al. in U.S. Pat. No. 5,470,748 and used in Hayden et al. U.S. Pat. No. 5,962,729 and Farmer U.S. Pat. No. 5,942,643 can be used to evaluate the activity of the carbon catalyst. In this determination, a catalyst sold under the trade name CENTAUR by Calgon exhibited a t-¾ of about 14 minutes. The remaining catalysts listed in Table 2 would exhibit a t-¾ value greater than 14 minutes.

In yet another form, the catalyst activity can be determined by an alternative method, i.e. using the hydrogen peroxide decomposition test described in Example 4. Under this method, the catalyst's activity is evaluated by the relative rate at which the different catalysts decompose hydrogen peroxide. In the test method, hydrogen peroxide decomposes and generates oxygen. The hydrogen peroxide decomposition rate is determined by measuring the pressure increase caused by the evolution of oxygen gas. The CENTAUR catalyst was the most active catalyst, and this catalyst was used as a standard against which the other catalysts were compared. Consequently, a peroxide activity factor was defined as the hydrogen peroxide half-life (in hours) divided by the packed bulk density (in $g/cm^3$) of the full-size carbon particles. This gives a peroxide decomposition factor that is inversely proportional to the intrinsic volumetric activity of a particular carbon. A catalyst for use in the present invention exhibits a hydrogen peroxide decomposition factor greater than about 0.80 hours/($g/cm^3$) as determined according to the procedure described in Example 4. More preferably the catalyst is selected to exhibit a hydrogen peroxide decomposition factor of greater than about 1.0, still more preferably greater than 8 hour/($g/cm^3$).

The following examples are presented to illustrate various aspects of the invention. They should not be construed as limiting the scope of the invention.

EXAMPLES

Example 1
Kinetic Modeling Experiments of PMG Synthesis

A ½" (1.27 cm) O.D. (0.402" (1.02 cm) I.D.) by 24" (61 cm) stainless steel 316 tube was used as the reactor. The reactor tube was jacketed with a 1" O.D. tube through which oil was continually circulated from a thermostatically controlled heating bath with an external circulation pump. The reactor was charged with about 4 g to about 9 g of carbon catalyst.

The reactor was operated in batch recycle trickle flow mode. A mixture of 40 g PMIDA in 1960 g of distilled water was pumped to the top of the reactor at about 60 mL/min using a positive displacement pump. Pure oxygen was also metered to the top of the reactor at a rate of approximately 380 sccm. The reactor pressure was maintained at approximately 7 atm (0.7 MPa) by passing the two-phase effluent through a back pressure regulator.

The reactor effluent was combined with the feed mixture in a stirred vessel (the mixer/feed vessel) maintained at 75° C. and ambient pressure. The gas effluent was vented through a water cooled condenser.

Figure 2:
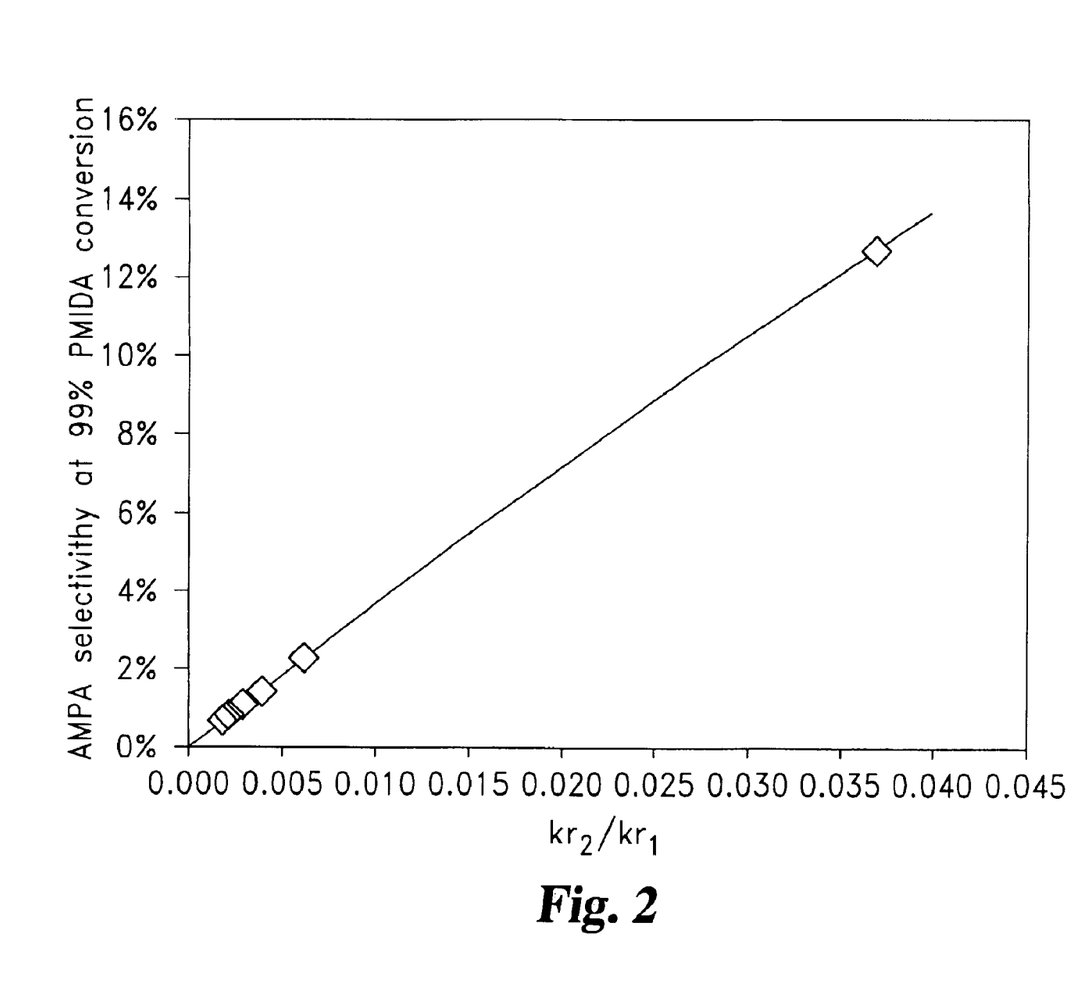
FIG. 2 is a graph illustrating the AMPA selectivity at 99% conversion of PMIDA compared to the ratio of the oxidation rate of PMG to the oxidation rate of PMIDA, ($k_{r2}/k_{r1}$).

The mixer/feed vessel was periodically sampled and analyzed for PMIDA, PMG, AMPA, MePMG, and MAMPA off-line using liquid chromatography. Each batch experiment was continued until the PMIDA concentration was lower than the lower detection limit of the analytical method, which indicated greater than 99% conversion of the initial PMIDA. FIG. 2 is a graph plotting $k_1/k_2$ verses AMPA selectivity for several different catalyst samples.

As described in the literature (N. Papayannako and J. Marangozis, *Chem. Eng. Sci.,* Vol. 39, No. 6, pp. 1051–1061, 1984), appropriate mathematical treatment of the experimental results will yield data useful for kinetic modeling. For each catalyst tested, this mathematical treatment was used to determine rate parameters for the PMG and AMPA formation reaction rate expressions in the kinetic model described above. These parameters were then used to predict the performance for each carbon under isothermal plug flow conditions. The results for seven different commercially available carbon catalysts are listed below in Table 3.

TABLE 3

| | | Kinetic Model Parameters | | | |
|---|---|---|---|---|---|
| Carbon Catalyst | Temp. ° C. | Pressure psig (Kpa) | $k_1$ (T) $(psi \cdot s)^{-1}$ | $k_2$ (T) $(psi \cdot s)^{-1}$ | $K_{PMIDA}$* L/mol |
| Calgon CENTAUR | 94.8 | 97.7 (774) | $1.28 \times 10^{-3}$ | $4.71 \times 10^{-5}$ | 41.0 |
| Calgon BCP | 94.1 | 90.5 (724) | $1.72 \times 10^{-2}$ | $6.66 \times 10^{-5}$ | 782 |

TABLE 3-continued

Kinetic Model Parameters

| Carbon Catalyst | Temp. ° C. | Pressure psig (Kpa) | $k_1$ (T) (psi · s)$^{-1}$ | $k_2$ (T) (psi · s)$^{-1}$ | $K_{PMIDA}$* L/mol |
|---|---|---|---|---|---|
| Norit PK | 95.2 | 93.9 (747) | $8.25 \times 10^{-3}$ | $2.40 \times 10^{-5}$ | 803 |
| Waterlink SE | 94.2 | 86.0 (693) | $9.97 \times 10^{-3}$ | $2.80 \times 10^{-5}$ | 803 |
| Waterlink 207A | 94.2 | 91.5 (731) | $1.68 \times 10^{-2}$ | $1.03 \times 10^{-4}$ | 782 |
| Sibunit 6 | 94.0 | 86.2 (694) | $4.29 \times 10^{-3}$ | $8.81 \times 10^{-6}$ | 803 |
| Nuchar RGC | 94.0 | 85.5 (689) | $1.09 \times 10^{-2}$ | $1.93 \times 10^{-5}$ | 782 |

*$K_{PMG}$ = 0 in all cases

Example 2
Continuous Steady-State Operation in a Laboratory Scale Trickle Bed

Experiments were conducted in a laboratory scale continuous trickle bed reactor. The reaction system was similar to that described in Example 1, except the reactor effluent was not returned to the feed mixing vessel. In each experiment, the reactor wall temperature was maintained at a constant value by continuously circulating hot oil through a jacket around the reactor, giving a nearly isothermal temperature in the catalyst bed. The catalyst bed contained 14.4 g of 20×50 mesh Nuchar RGC activated carbon catalyst. Experiments were conducted at various temperatures and liquid feed rates. The reactor pressure was 100 psia (689 KPa), and the oxygen flow rate was 200 sccm. The aqueous feed consisted of 2 weight % PMIDA and, optionally, 3.02 weight % PMG. The experiments with the additional PMG were used to simulate a partially converted 6 weight % PMIDA feed. For samples 1 and 2, the molar selectivities and fractional conversion are based on the simulated feed of 6 weight % PMIDA. The results are listed in Table 4, below. These data are GC results, normalized and then converted to molar selectivities and conversions.

TABLE 4

| Sample | T (° C.) | Liquid feed rate mL/min | PMIDA Feed (wt. %) | PMG Feed (wt. %) | AMPA molar selectivity | MePMG molar selectivity | PMG molar selectivity | PMIDA fractional conversion |
|---|---|---|---|---|---|---|---|---|
| 1 | 115.5 | 32.0 | 2.0 | 3.02 | 0.94% | 0.06% | 99.00% | 99.99% |
| 2 | 115.5 | 40.0 | 2.0 | 3.02 | 0.19% | 0.07% | 99.75% | 98.86% |
| 3 | 115.5 | 30.0 | 2.0 | 0.0 | 0.20% | 0.10% | 99.69% | 99.26% |
| 4 | 104.5 | 21.0 | 2.0 | 0.0 | 0.19% | 0.17% | 99.64% | 99.28% |
| 5 | 104.5 | 21.0 | 2.0 | 0.0 | 0.00% | 0.35% | 99.65% | 99.55% |
| 6 | 115.5 | 30.7 | 2.0 | 0.0 | 0.19% | 0.07% | 99.74% | 99.50% |
| 7 | 115.5 | 30.5 | 2.0 | 0.0 | 0.36% | 0.06% | 99.58% | 99.72% |

Example 3
Evaluation of Catalysts Having Different Average Particle Sizes

Table 5 below lists the performance of two different particle sizes of the same carbon, Calgon CENTAUR, at 95° C. reactor temperature, evaluated using the kinetic model procedure described earlier. A smaller average particle size was obtained from an unused portion of the Calgon CENTAUR listed in Table 3 by crushing and sieving. The resulting crushed Calgon CENTAUR in Table 5 had a particle size range of 80 to 100 mesh (149–177 μm). These data demonstrate that smaller particles of the same carbon material can be used to achieve lower values of α and, therefore, improved selectivity.

TABLE 5

| Carbon Catalyst | Mesh (μm) | α | AMPA selectivity at 99% PMIDA conversion | Maximum PMG yield |
|---|---|---|---|---|
| Calgon CENTAUR | 20 × 50 (297–840) | 0.0369 | 12.6% | 88.1% |
| Calgon CENTAUR | 80 × 100 (149–177) | 0.0017 | 0.6% | 98.6% |

Example 4
Rate of Hydrogen Peroxide Decomposition by Carbon Catalyst

Activated carbons are known to catalyze the decomposition of hydrogen peroxide in aqueous solutions. [Smith, R. N., A. J. Miles, and S. F. Watkins, "Carbon-Catalyzed Decomposition of Hydrogen Peroxide," *Faraday Soc. Trans.*, 62, 2553–65 (1966).] The rate of hydrogen peroxide decomposition over seven carbon catalysts listed above in Table 1 in a closed, isothermal system was determined according the following procedure:

Reaction progress was measured by monitoring the pressure rise due to evolution of oxygen from a buffered aqueous slurry. The experimental conditions were as follows: a stainless steel reactor (HP100 from Mettler) having a total volume of about 1800 cm$^3$ was charged with 0.5 g carbon, crushed and sieved to smaller than 325 mesh (<44 μm), 800 g of water, 110 g 0.5 M $K_2HPO_4$/0.5 M $KH_2PO_4$, and 140 g of 30 wt. % $H_2O_2$ (in water). The reactor was closed and sealed to provide a leak tight system. The peroxide decomposition reaction was conducted under isothermal conditions at 25° C. using 200 rpm stirrer speed and at an initial pressure of 0.0 bar (The reactor was vented and then sealed immediately after peroxide addition.) It should be noted that the carbon particles were crushed and sieved so that only those particles smaller than 325 mesh (<44 μm) were used in the peroxide decomposition experiment. In this way, any potential pore diffusion effects should be avoided, with the experimental results directly indicating the intrinsic activity of the catalyst.

The peroxide half-life under these conditions was defined as the time required to reach a pressure of 10.6 bar (1.06 MPa). This value was determined to be 50% of the final pressure achieved in the test with the most active carbon, i.e., Calgon CENTAUR, which completely decomposed the peroxide in only a few hours. The rate of hydrogen peroxide decomposition over seven carbon catalysts was determined according to this procedure; the results are listed below in Table 6.

TABLE 6

Rate of Hydrogen Peroxide Decomposition by Carbon Catalyst

| Carbon Catalyst | Half-life/Bulk density (hours/(g/cm$^3$)) |
|---|---|
| Centaur | 0.82 |
| Waterlink 207A | 6.9 |
| Calgon BCP | 15.8 |
| Norit PK | 18.0 |
| Waterlink SE | 249 |
| Sibunit 6 | 229 |
| Nuchar RGC | 306 |

The peroxide test used a constant mass of carbon catalyst. However, the transport effects in a fixed bed process are volumetric in nature. Consequently, a peroxide activity factor was defined as the hydrogen peroxide half-life (in hours) divided by the packed bulk density (in g/cm$^3$) of the full-size carbon particles. This gives a peroxide decomposition factor that is inversely proportional to the intrinsic volumetric activity of a particular carbon.

The selection of suitable catalysts in conjunction to the conditions under which the catalyzed oxidation reaction is performed can impact the yield and purity of the desired PMG product. Improved yields can be obtained by minimizing the rate of reaction for the competing side reactions and/or by-products while maximizing the rate of PMIDA oxidation to PMG.

The present invention contemplates modifications as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A continuous process for the production of glyphosate, said process comprising:

contacting N-phosphonomethyliminodiacetic acid with molecular oxygen in the presence of a carbon catalyst supported in a fixed bed reactor under conditions which oxidize N-phosphonomethyliminodiacetic acid to glyphosate and oxidize glyphosate to (aminomethyl) phosphonic acid; and selecting a carbon catalyst for use in the process whereby a ratio of a rate constant of reaction of glyphosate with molecular oxygen to a rate constant of reaction of N-phosphonomethyliminodiacetic acid with molecular oxygen is less than about 0.017.

2. The process of claim 1, wherein the ratio of the rate constant of the reaction of glyphosate with molecular oxygen to the rate constant of the reaction of N-phosphonomethyliminodiacetic acid with molecular oxygen is less than about 0.008.

3. The process of claim 1, wherein the ratio of the rate constant of the reaction of glyphosate with molecular oxygen to the rate constant of the reaction of N-phosphonomethyliminodiacetic acid with molecular oxygen is less than about 0.004.

4. The process of claim 1 wherein said contacting is performed at a temperature level of at least about 75° C.

5. The process of claim 1 wherein the carbon catalyst that is selected exhibits a peroxide decomposition factor of greater than about 1 hour/(g/cm$^3$).

6. The process of claim 1 wherein the carbon catalyst that is selected exhibits a peroxide decomposition factor of greater than about 0.8 hour/(g/cm$^3$).

7. The process of claim 1 wherein the carbon catalyst that is selected has an average particle size of between about 150 and about 3000 micrometers.

8. The process of claim 7 wherein the carbon catalyst that is selected has an average particle size of between about 250 and about 1000 micrometers.

9. The process of claim 7 wherein the carbon catalyst that is selected exhibits a peroxide decomposition factor of greater than about 8 hour/(g/cm$^3$).

10. The process of claim 1 wherein N-phosphonomethyliminodiacetic acid is provided as a saturated aqueous solution.

11. The process of claim 1 wherein N-phosphonomethyliminodiacetic acid is provided in a concentration of between about 2 wt % and about 10 wt% in an aqueous solution.

12. The process of claim 1 wherein the process is conducted at a pressure of between about 3.5 atm and about 20 atm.

13. The process of claim 1 wherein greater than about 95 molar % of the N-phosphonomethyliminodiacetic acid is consumed.

14. The process of claim 13 wherein the carbon catalyst that is selected exhibits a peroxide decomposition factor of greater than about 1 hour/(g/cm$^3$).

15. The process of claim 14 wherein the carbon catalyst that is selected exhibits a peroxide decomposition factor of greater than about 8 hour/(g/cm$^3$).

16. The process of claim 1 wherein the N-phosphonomethyliminodiacetic acid and the molecular oxygen are combined in a reaction mixture, said mixture provided to sequentially flow through two or more fixed bed reactors connected in series.

17. A continuous process for the production of glyphosate, said process comprising:

contacting N-phosphonomethyliminodiacetic acid with molecular oxygen in the presence of a carbon catalyst supported in a fixed bed reactor under conditions which oxidize N-phosphonomethyliminodiacetic acid to glyphosate in greater than about 93% molar yield and oxidize glyphosate to (aminomethyl)phosphonic acid; and selecting a carbon catalyst for use in the process whereby a ratio of a rate constant of reaction of glyphosate with molecular oxygen to a rate constant of reaction of N-phosphonomethyliminodiacetic acid with molecular oxygen is less than about 0.017.

18. A continuous process for the production of glyphosate, said process comprising:

contacting N-phosphonomethyliminodiacetic acid with molecular oxygen in the presence of a carbon catalyst supported in a fixed bed reactor under conditions which oxidize N-phosphonomethyliminodiacetic acid to glyphosate and oxidize glyphosate to (aminomethyl) phosphonic acid; and conducting the process whereby a ratio of a rate constant of reaction of glyphosate with molecular oxygen to a rate constant of reaction of N-phosphonomethyliminodiacetic acid with molecular oxygen is less than about 0.017.

19. A continuous process for the production of glyphosate, said process comprising:

contacting N-phosphonomethyliminodiacetic acid with molecular oxygen in the presence of a carbon catalyst supported in a fixed bed reactor under conditions which oxidize N-phosphonomethyliminodiacetic acid to glyphosate in greater than about 93% molar yield and oxidize glyphosate to (aminomethyl)phosphonic acid; and conducting the process whereby a ratio of a rate constant of reaction of glyphosate with molecular oxygen to a rate constant of reaction of N-phosphonomethyliminodiacetic acid with molecular oxygen is less than about 0.017.

* * * * *